United States Patent
Hartung et al.

(10) Patent No.: US 9,036,880 B2
(45) Date of Patent: May 19, 2015

(54) HIGH-RESOLUTION THREE-DIMENSIONAL MEDICAL IMAGING WITH DYNAMIC REAL-TIME INFORMATION

(75) Inventors: Ulrich Hartung, Langensendelbach (DE); Matthias John, Nürnberg (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 1098 days.

(21) Appl. No.: 12/797,759

(22) Filed: Jun. 10, 2010

(65) Prior Publication Data

US 2010/0316278 A1    Dec. 16, 2010

(30) Foreign Application Priority Data

Jun. 12, 2009  (DE) .......................... 10 2009 024 652

(51) Int. Cl.
*G06K 9/00* (2006.01)
*A61B 6/03* (2006.01)
(Continued)

(52) U.S. Cl.
CPC ................ *A61B 6/032* (2013.01); *A61B 6/466* (2013.01); *A61B 6/5247* (2013.01); *A61B 8/08* (2013.01); *A61B 8/0841* (2013.01); *A61B 8/483* (2013.01); *A61B 8/5238* (2013.01); *A61B 5/7285* (2013.01); *A61B 6/12* (2013.01); *A61B 6/4441* (2013.01); *A61B 6/503* (2013.01); *A61B 6/504* (2013.01); *A61B 6/541* (2013.01); *A61B 8/0833* (2013.01);
(Continued)

(58) Field of Classification Search
CPC .......... G06K 9/00369; G06K 9/00127; G06K 9/6269; G06K 9/62; G06K 9/00624; G06K 9/4642; G06K 2209/057; G06T 5/001; G06T 7/0014; G06T 7/2033; G06T 2207/10072; G06T 2207/10081; G06T 2207/10116; G06T 7/0044

See application file for complete search history.

(56) References Cited

U.S. PATENT DOCUMENTS 6,923,768 B2  8/2005  Camus
7,689,019 B2  3/2010  Boese et al.
(Continued)

FOREIGN PATENT DOCUMENTS

DE    10210650 B4    4/2005
DE    10340546 B4    4/2006
(Continued)

OTHER PUBLICATIONS

Biosense Webster Inc.; Carto XP EP Navigation System; http://www.biosensewebster.com/products/navigation/cartoxp.aspx; Diamond Bar, CA; Biosense Webster, Inc.; Others; 2006; US.
(Continued)

*Primary Examiner* — Maroun Kanaan
(74) *Attorney, Agent, or Firm* — Harness, Dickey & Pierce P.L.C.

(57) ABSTRACT

A computer-implemented method, a device, a system and a computer program are disclosed for three-dimensional displaying of medical body structures within the framework of a medical procedure, in particular cardiac surgery, wherein movement information is derived from a dynamic image of a body structure to be examined. In at least one embodiment, movement information is derived from vector analysis. After acquiring a static image of the respective body structure, vector analysis is applied to the static image to derive a modified static image with movement information of the body structure. The static image can then be displayed after it has moved.

23 Claims, 3 Drawing Sheets

(51) Int. Cl.
*A61B 6/00* (2006.01)
*A61B 8/08* (2006.01)
A61B 5/00 (2006.01)
A61B 6/12 (2006.01)
A61B 8/00 (2006.01)
A61B 19/00 (2006.01)
G01R 33/48 (2006.01)
G01R 33/563 (2006.01)

(52) U.S. Cl.
CPC ......... *A61B 8/543* (2013.01); *A61B 2019/5289* (2013.01); *G01R 33/4808* (2013.01); *G01R 33/56308* (2013.01)

(56) References Cited

U.S. PATENT DOCUMENTS

| | | | |
|---|---|---|---|
| 8,364,242 | B2* | 1/2013 | Li ................................ 600/424 |
| 2003/0199748 | A1 | 10/2003 | Camus et al. |
| 2004/0030246 | A1 | 2/2004 | Townsend et al. |
| 2004/0143189 | A1 | 7/2004 | Lysyansky |
| 2006/0078183 | A1* | 4/2006 | deCharms .................... 382/128 |
| 2006/0262970 | A1 | 11/2006 | Boese et al. |
| 2007/0027390 | A1 | 2/2007 | Maschké et al. |
| 2007/0276243 | A1 | 11/2007 | Florent |
| 2007/0287902 | A1 | 12/2007 | Fuimaono et al. |
| 2010/0002929 | A1* | 1/2010 | Sammak et al. ............ 382/133 |

FOREIGN PATENT DOCUMENTS

| | | |
|---|---|---|
| DE | 102005032755 A1 | 1/2007 |
| DE | 102005046410 A1 | 4/2007 |
| DE | 102005023167 B4 | 1/2008 |

OTHER PUBLICATIONS

Prospekt der Firma Siemens medical: "Axius Velocity Vector Imaging", 2006; Others; 2006.

* cited by examiner

HIGH-RESOLUTION THREE-DIMENSIONAL MEDICAL IMAGING WITH DYNAMIC REAL-TIME INFORMATION

PRIORITY STATEMENT

The present application hereby claims priority under 35 U.S.C. §119 on German patent application number DE 10 2009 024 652.5 filed Jun. 12, 2009, the entire contents of which are hereby incorporated herein by reference.

FIELD

At least one embodiment of the present invention generally relates to a computer-implemented method, to a system, to a device and/or to a computer program for three-dimensional displaying of medical body structures within the framework of medical interventional procedures, such as electrophysiological operations or heart surgery or other operations on the human or animal body.

BACKGROUND

In many fields of modern medicine, in particular in the field of cardiology, imaging methods are increasingly being used in minor and more complex clinical procedures.

The imaging methods are basically used firstly for orientation in the body structure during the operative procedure and secondly to locate medical instruments, which are required within the framework of the operative procedure (such as a catheter in the case of heart surgery, or surgical instruments), in exactly the correct position. Another example is the exact positioning of an aortic valve prosthesis in a cardiological operation. These methods are also used in diagnostics, moreover.

The imaging methods can be classed in different categories. Thus, on the one hand there is two-dimensional imaging. These modalities acquire two-dimensional images. This includes fluoroscopy which, for example, produces a continuous film of two-dimensional X-ray images in real time.

A further category relates to three-dimensional imaging to generate three-dimensional images. This includes, for example, C-arm CTC-arm CT. This method involves rotational angiography with three-dimensional image reconstruction during the intervention on X-ray C-arms. Other examples of three-dimensional imaging methods are known in the prior art (for example CT, MR, etc.).

In addition to the above classification into two-dimensional and three-dimensional imaging methods, these methods may also be categorized according to the degree of resolution. There are therefore high-resolution methods and less high-resolution methods. The high-resolution methods are distinguished by a very high level of detail. These methods are conventionally static, however, and during an operation do not provide the operator or examiner with any information about the respective body structures being examined in relation to time. Movement information cannot be derived from the static images therefore. The static imaging methods are conventionally used pre-operatively.

In addition to the static methods there are the dynamic imaging methods which include a time reference. These methods include, for example, ultrasound, in particular cardiac ultrasound, optical methods (for example methods in which a camera is introduced into an organ in order to acquire images), infrared techniques and radioscopy. It is likewise possible to generate dynamic images using magnetic resonance tomographs and computed tomographs.

The need for high-resolution real-time methods for three-dimensional imaging is growing constantly in the field of interventional medicine. Procedures with this requirement, such as a transfemoral aortic valve replacement, are increasingly being carried out in particular in the field of cardiology. Atrial fibrillation has been treated with the aid of sclerotherapy procedures within the left atrium for a relatively long time already in the field of electrophysiology.

That the imaging is either not dynamic (for example C-arm CTC-arm CT) or that the imaging does not reproduce the current state of the patient (for example computed tomography), or that the acquired images do not have the required spatial resolution (such as ultrasound, electro-anatomical mapping, etc.), or that they do not generally provide three-dimensional images has proven to be problematic in the known imaging methods.

SUMMARY

In at least one embodiment of the present invention is directed to a method with which dynamic information, in particular information with a time reference in relation to the body structure to be examined, can be integrated in high-resolution and detailed static imaging, wherein the imaging can also be used intraoperatively or intraprocedurally.

The solution in relation to the method will be described hereinafter. Here, mentioned features, advantages or alternative embodiments should also be transferred to the other claimed subject matters and vice versa. In other words, the objective claims (which are directed toward a system or a device for example) can also be developed using the features described or claimed in connection with the method. The corresponding functional features of the method are formed by corresponding objective modules, in particular by hardware modules, of the system or device.

At least one embodiment is directed to a computer-implemented method for displaying medical body structures in the field of interventional medicine and in particular within the framework of heart surgery or another procedure, comprising the following method steps:
  acquiring a static image of the body structure in high resolution,
  carrying out dynamic imaging to acquire a dynamic image,
  carrying out vector analysis on data records of the dynamic image to acquire movement information of the body structure,
  applying the vector analysis to the static image to calculate a modified static image with movement information of the body structure,
  displaying the modified static image with associated movement information of the body structure.

In other words, a fundamental aspect of at least one embodiment of the present invention relates to combining the advantages of high-resolution static imaging with dynamic imaging with lower resolution. The inventive approach of at least one embodiment offers the possibility of the examiner being able to fall back on dynamic real-time 3D imaging even during the medical procedure or medical operation in order to plan and/or control the further course of the operation. The concepts used within the framework of at least one embodiment of the present invention will be specified in more detail hereinafter.

The "body structures" are in particular structures in the human body that are relevant to the respective medical examination. They may be sections of the heart or the whole heart here by way of example. Further examples are all types and forms of complex electrophysiological procedures or abdominal vascular surgery procedures. However, it is not imperative to the present invention for an operative procedure to always be carried out. The inventive approach may also be applied to diagnostic methods or pre-operative methods. The wording "interventional medicine" is used here as a generic term.

The term "static image" should be taken to mean all imaging methods for acquiring images which are conventionally in high resolution, very detailed and do not include a time reference (and therefore no dynamic information). Examples of static imaging methods are computed tomography and C-arm CT. Alternatively, MR methods or other functional imaging methods may be used here. They can be in the form of a 2D or 3D image data record.

The term "dynamic imaging" should be taken to mean all imaging methods which include a dynamic aspect. The dynamic imaging methods include, in particular, ultrasound, in particular cardiac ultrasound, and electro-anatomical mapping. Alternatively, MR methods may likewise be used here, however. The dynamic images may also be in the form of a 2D or 3D image data record.

According to an example embodiment of the present invention both the static image and the dynamic image are three-dimensional images. Alternatively, two-dimensional imaging methods may optionally also be individually or cumulatively used here, however. In other words, the static image and/or the dynamic image can also be in two-dimensional form. An example of a two-dimensional dynamic imaging method is fluoroscopy and, primarily, ultrasound.

The term "vector analysis" should be taken to mean a technique by which individual body segments can be quantitatively analyzed in terms of their movement (movement direction and movement speed). In the field of ultrasound technology this method has been developed under the name "Axius Velocity Vector Imaging—VVI" by Siemens Medical Solutions in Erlangen. In the case of this method ultrasound data is used for visually displaying the heartbeat mechanism, so the physician can be provided with information relating to the mechanism of heart contraction. Basically this technology can, however, be applied not only to the field of heart surgery but to all medical fields. According to at least one embodiment of the invention vector analysis is applied to the data records of the dynamic image to acquire movement information of the body structure (for example the heart). The movement information obtained in this way is then extracted from the dynamic image and embedded or integrated in the static, high-resolution image.

Application of vector analysis presupposes that a one-to-one relationship can be calculated and provided between the static image and the dynamic image. In a more detailed embodiment the method includes a further method step prior to the step of application. This relates to a registration of the image data records from a spatial and/or time-related perspective. This is used to be able to reference the two data records in relation to each other.

In an example embodiment, individual points in the respective image or the respective data records are correlated in relation to a time axis. The ECG is preferably used as the time axis and reference point in this connection. However, it is also possible for other reference points to be chosen here in order to be able to generate a "mapping", as it were, between the data of the dynamic image and the data of the static image. As the three-dimensional static image usually comprises significantly more matrix or image points than the dynamic image (which conventionally exists in a lower resolution), the reference points for which no vector information exists are interpolated in the dynamic image.

In an example embodiment of the invention, it is provided that the static image is acquired before a procedure, i.e. pre-operatively. The dynamic image is conventionally acquired, provided and displayed during a medical procedure. Alternative embodiments can, however, also provide that the static image is also acquired during the medical procedure. Within the framework of a medical diagnosis it may also be the case that the static image and/or the dynamic image is/are not acquired within the framework of a medical procedure but is/are only acquired for diagnostic purposes.

According to one aspect of at least one embodiment of the invention, the method is only applied to surfaces of body structures. This has the advantage that only surface are dynamized.

In a variant of at least one embodiment of the invention, it is provided that displaying the modified static image provides navigation information. It is possible to control the operative procedure using the navigation information. In particular the surgical instruments can be accurately positioned and relevant body structures can be located. Fully automatic, computer-assisted positioning of operative equipment is also possible. The displayed modified static image can also be used to identify and locate medical instruments (such as an intracardiac catheter) in the body structure to be examined. On the one hand it is therefore possible to check the position of an intracardiac catheter that has already been implemented and on the other hand it is possible to exactly position and control re-insertion of an intracardiac catheter within the framework of an interventional procedure.

As has already been mentioned above, an example embodiment of the invention relates to the case where both the static image and the dynamic image are in the form of a three-dimensional data record. Two-dimensional data records provide alternatives to the static image and/or the dynamic image here, however.

Since one aspect is directed toward control of an interventional procedure, dynamic imaging is preferably carried out in real time. This provides the fundamental advantage of it being possible to position and control the medical structures (such as intracardiac catheters, OP instruments, etc.) completely automatically within the framework of an operative procedure.

According to one aspect of at least one embodiment of the present invention the static image is a computed tomography or a C-arm computed tomography. The dynamic image is conventionally an ultrasound image, for example of the heart. It is preferably a three-dimensional ultrasound image.

According to one aspect of at least one embodiment of the present invention, individual steps of at least one embodiment of the above-mentioned method may also be carried out iteratively and therefore repeatedly. In particular it is possible to carry out vector analysis on the dynamic image again, to apply carried out vector analysis again and therefore repeatedly to the static image and to likewise display the modified static image again and repeatedly. This has the advantage that renewed analysis is possible if anything changes in terms of the movement, without a new three-dimensional C-arm CT picture having to be acquired. Changes can occur, for example, due to the administering of medicines or within the framework of the operation.

According to an advantageous embodiment, the method is carried out in a computer-assisted manner, is triggered and/or controlled semi-automatically or fully automatically. This means that it is automatically detected whether static and dynamic images exist for a body structure. The physician can then be asked via a provided user mask whether he wants the combination of the two data records. Otherwise the combination of data records is automatically provided.

According to one aspect of at least one embodiment of the invention, it is possible to rework the modified static image. This is particularly advantageous for example if the automatically displayed, modified static image requires manual adjustments at individual points. For example it can be expedient to adjust individual reference points to optimize overlaying or embedding from the dynamic image into the static image. This is preferably done manually by the examiner. However, it is also possible for the physician to be assisted in this connection. Manual or automatic adjustment of sizes constitutes a different type of reworking. Accentuations (colored formations or the like) also lie within the framework of possible reworking steps.

In at least one embodiment, a system is disclosed for displaying medical body structures in the field of interventional medicine, comprising:
- at least one static modality for generating static images,
- at least one dynamic modality for generating dynamic images,
- at least one calculating module for carrying out vector analysis on the dynamic image to acquire movement information of the body structure, the information then being applied to the static image to calculate a modified static image with movement information of the body structure,
- at least one display device for displaying the modified static image with associated movement information of the body structure, as is provided by the calculating module.

The calculating module conventionally exchanges data with the static and the dynamic modalities and with the display device. In a simple variant of at least one embodiment of the invention this data exchange is unidirectional, however, so only the transmission of the image data acquired by the respective modalities to the calculating module is configured.

The calculating module can also be constructed with an internal or external memory for storing the vector analysis. The result of vector analysis can therefore also be used externally and separately, as it were, for example for other purposes.

In at least one embodiment, a device is disclosed for displaying medical body structures in the field of interventional medicine, comprising:
- at least one calculating module which exchanges data with a static modality and with a dynamic modality and which is configured to carry out vector analysis on data records of the dynamic image to acquire movement information of the body structure and which is configured to apply the vector analysis to the static image to calculate a modified static image with movement information of the body structure.

The calculating module can preferably exchange data with a monitor to display the modified static image on the monitor.

In at least one embodiment, a computer program is disclosed which is configured to carry out the above-described method if the commands are executed on the computer, and the program is loaded in the computer.

It is also possible for individual components of the above-described method to be constructed in a saleable unit and for the remaining components to be constructed in another saleable unit—as a distributed system so to speak. The calculating instance can therefore be configured as a component of one of the static or dynamic modalities, added to the network as a separate instance or be integrated as a module in a client/server solution.

BRIEF DESCRIPTION OF THE DRAWINGS

The following detailed description of the figures addresses example embodiments and their features and further advantages with reference to the drawings in a non-limiting manner. In the drawings.

DETAILED DESCRIPTION OF THE EXAMPLE EMBODIMENTS

Figure 1:
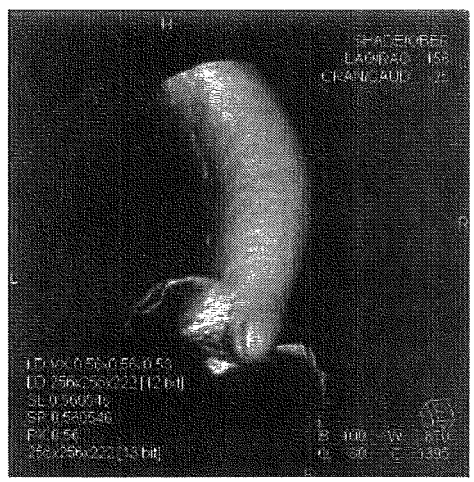
FIG. 1 shows a schematic view of static imaging according to an example embodiment using an example.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the present invention relates to the intelligent combination of dynamic imaging with low resolution and static high-resolution imaging. Movement information on the structure being examined is evaluated and/or extracted from the dynamic imaging, with which information the high-resolution (but statically recorded) image is moved.

Using an example FIG. 1 shows a static image S which was acquired using a C-arm CT. The Dyna CT from Siemens is an example of a C-arm modality. The example illustrated in FIG. 1 shows a static three-dimensional reconstruction of the aortic bulb with Aorta ascendens and beginning of the coronary arteries in the lower region. The static image S is therefore conventionally acquired used a CT or Dyna CT modality.

Figure 2:
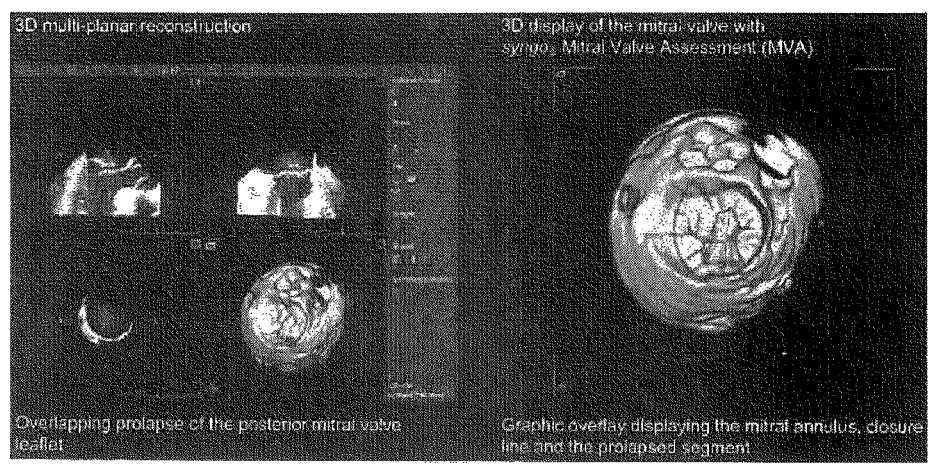
FIG. 2 shows an exemplary view of dynamic imaging using the example of a transesophageal ultrasound data record.

Using an example FIG. 2 shows a three-dimensional dynamic image D using the example of a display from a transesophageal ultrasound data record. In this example the mitral valve in the case of a mitral valve prolapse is in focus (right-hand image). The ultrasound data record is conventionally in a lower resolution and has higher noise compared with X-ray imaging. Other dynamic imaging methods may also be used in addition to an ultrasound modality for acquiring the dynamic image D, such as optical methods, infrared and radioscopy as well as MR and CT modalities.

Figure 4:
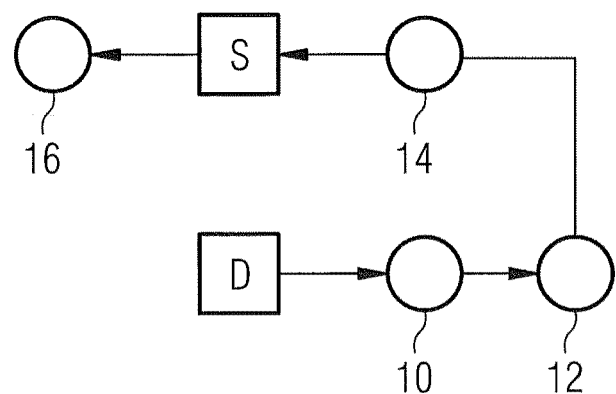
FIG. 4 shows a schematic view of a typical progression of the inventive method according to an example embodiment.

FIG. 4 shows a typical progression according to an example embodiment of the inventive method. An example embodiment of the inventive method is based on acquiring the dynamic image D and the static image S. Alternatively, several acquisition processes may also be included here. A dynamic imaging method for acquiring the dynamic image D is conventionally carried out during an operative procedure or in preparation for the same.

A vector analysis is applied to the data records of the dynamic image D in step 10. Vector analysis is used to acquire movement information of the body structure to be examined.

Movement information relating to dynamic image D is provided in step 12.

The provided movement information is applied to the static image S in step 14. This means that the static image S can be moved using the acquired movement information.

The static image S, moved using the movement information, is shown on a monitor M as a modified static image in step 16.

One aspect of an embodiment of the present invention therefore relates to the embedding of the acquired movement information from the dynamic image D in the static image S, so the static image S can be moved according to the real-time specifications. The advantages of high-resolution but static imaging can therefore be combined with the advantages of dynamic imaging in lower resolution.

An alternative solution of an embodiment resides in a system which is computer-implemented and is intended for three-dimensional display of medical body structure within the framework of interventional medicine. The system comprises a static modality tor generating static images S and a dynamic modality for generating dynamic images D, and a calculating module 18 for carrying out vector analysis on the data records of the dynamic image D to acquire movement information of the body structure to be examined. The system also conventionally (but optionally) comprises a display device, in particular a monitor M, for displaying the modified static image which is moved using the specifications of vector analysis. The information for moving the image is provided by the calculating module 18.

Figure 5:
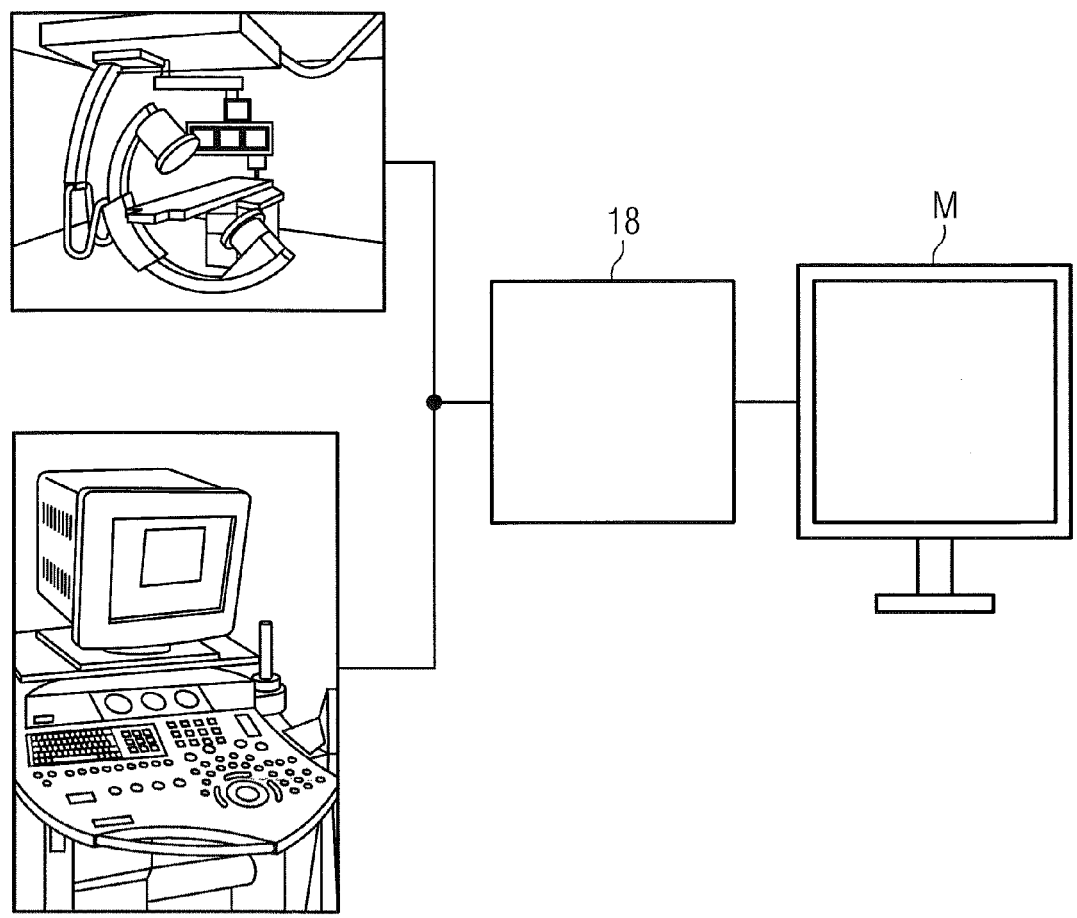
FIG. 5 shows a view of a basic structure of the inventive system according to an example embodiment.

FIG. 5 shows in a schematic view a system of this kind, the static modality for acquiring the static image S being shown top left and the dynamic modality for acquiring the dynamic image D being shown bottom left. Both data records are acquired and supplied to the calculating module 18 which by means of vector analysis derives movement information from the dynamic image D to display the modified static image after it has moved. Display takes place on the monitor identified by reference character M.

Figure 3:
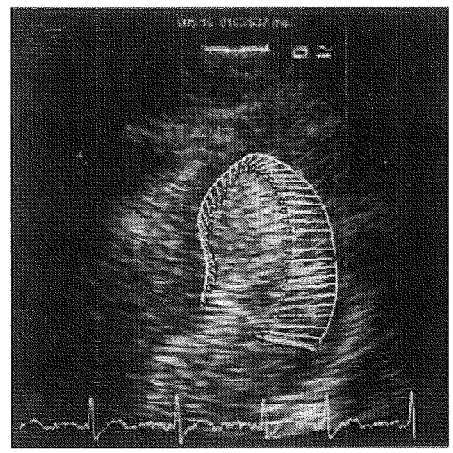
FIG. 3 shows a view of a dynamic image with associated and provided movement information.

FIG. 3 shows in an example view a dynamic image in which movement information is provided. As a result of the method the modified static image is shown as a dynamic, i.e. a moved, image. It is based on the high-resolution data records of the static image S and is moved according to the specifications of the dynamic image D. FIG. 3 shows in detail the display of the dynamic heart ultrasound image using the example of vector analysis of the left ventricle. The bottom region of FIG. 3 shows the ECG which serves as the time axis and reference in this case.

An important advantage and fundamental aspect of an embodiment of the present invention can be seen in that the modified static image can be displayed in real time, so it can be used for control purposes even during an examination. In contrast to previous methods known from the prior art the real-time information can be used to display an intracardiac catheter in relation to the anatomy of the heart in real time as well, so said intracardiac catheter may be correctly positioned without a separate X-ray examination having to be used.

A further advantage of an embodiment compared with systems from the prior art can be seen in that the (preferably) three-dimensional dynamic information is accordingly also available in high-resolution form, as a moved C-arm CT image as it were, and therefore makes the treatment or operation considerably easier for the physician. A further aspect can be seen in the real-time processing. This is a particularly important advantage as the course of the procedure makes it possible for the examiner to be able to navigate and control the device in real time even during the operation.

According to an embodiment of the invention therefore the pre-operatively acquired static data record moves using the movement information from the three-dimensional echo data record. In preparation the dynamic (for example ultrasound) image can also be displayed with the movement information that has been derived from vector analysis. FIG. 3 shows this movement information as vectors overlaid on the image. These vectors are then applied to the high-resolution static image S. The moved (and therefore no longer static) image is shown on the monitor M. The 3D imaging is therefore merged in real time with the static detailed 3D imaging of the C-arm CT. The dynamic information content (i.e. the real-time information) is obtained from the ultrasound data and added to or superimposed on the C-arm CT image.

Referencing of the two images S, D is required in order to be able to move the static image S using the information from the dynamic image D. This process is also called registration. Registration is preferably initiated semi-automatically by, for example, acquiring and allocating a plurality of exactly matching fixed points or reference points within the two data records S, D. Alternatively, edges in the image data can be used for registration, as is already known in the prior art and has been applied for by the applicant in a separate patent application. Another alternative to registration is the use of a position recognition system on the ultrasound device. This position recognition is also known in the prior art and is based on another separate patent application by the applicant. In this case the position sensor for example is used on the basis of electromagnetic position finding. The locating system and the X-ray system must be registered so that overlaying of the images D, S can be calculated.

The ultrasound data includes a time reference or time data (where possible in real time). Movement information can be derived from this data by means of vector analysis, in particular by way of the WI method. The movement vector includes a speed content and a direction content in relation to the respective movement of the body structure to be examined. The movement of the body structure to be examined can therefore be described in real time. This movement information is applied to the static image S. By overlaying the images S, D these vectors can be applied to the C-arm CT data record S. From this a dynamic, high-resolution three-dimensional data record (with integrated movement information) can be displayed. In other words, by allocating the movement information to the corresponding C-arm CT data the static C-arm CT model is dynamized.

In an example embodiment, it is provided that firstly the static image S is acquired and that during the operation dynamic imaging for acquiring the dynamic image D is carried out. Alternatively, a different sequence of methods steps is possible here, however. In particular it is also possible to acquire the dynamic image D during the operation and to then acquire the static image S, i.e. at a later instant, which static image should then be displayed in a modified, namely moved, manner.

According to one aspect of an embodiment of the invention it is possible for a target region to be determined before acquiring the images S, D, the target region being determined as the body structure to be examined. The body structure to be examined is then acquired by way of conventional CT or C-arm CT imaging. It is possible to determine certain time triggers for image acquisition in this case. For example, the end of a diastole can be determined in procedures inside the main chambers of the heart.

Alternatively, the end of the systole is possible as a time trigger in procedures focusing on the atriums. In both cases the largest size of the anatomical body structure respectively is taken into account. A movement field of the target region or the body structure can then be determined. This can be carried out for example by a sequence of 3D ultrasound data with its analysis of the movement vectors. The vectors determined at the respective reference points are inserted in the C-arm CT data record in correlation to a time axis. The ECG can be used in the case of the time axis. Alternatively, it is possible to provide a reference time axis. Manual mapping may likewise be necessary if a corresponding time structure cannot be determined.

Referencing of the two images S, D in relation to time can take place automatically or manually. With cardiac applications both static and dynamic images include an ECG signal which describes the cardiac phase and is therefore used for the registration over time. The other important movement—breathing—can also be measured and recorded in a parallel manner.

In both cases the registration over time is then automatically possible. With automatic referencing basically corresponding fixed points are identified within the two image data records S, D. With manual referencing the physician assumes this allocation function. The physician can advantageously be assisted in this process by a computer-assisted interface.

Finally, the registered movement field is applied to the static 3D structure. This can take place for example by integration of the vector movement over time in the C-arm CT overall reconstruction. This process includes a computer-assisted, and therefore automatic, interpolation of all 3D matrix points or reference points within the merged (and therefore displayed after they have moved) C-arm CT data record for which no vector information exists.

An important aspect of an embodiment of the invention may also be seen in the fact that only surfaces of body structures are dynamized. Displaying can therefore be significantly accelerated.

The moved three-dimensional structure is displayed in a final step.

A further advantage of an embodiment of the inventive solution can be seen in that the modified static image can be reworked. In other words, it is therefore possible to carry out determination of the movement field of the target region, registration of the data and application of the registered movement field to the static structure as well as visual display of the moved structure repeatedly. It is therefore possible to make relatively minor corrections when overlaying the two image data records S, D. This is expedient for example if the physician recognizes that anomalies are shown when the modified static image is displayed overlaid, the anomalies resulting for example due to incorrect referencing. The physician can then manually adjust certain points. This preferably takes place in real time and with a maximum delay of 200 milliseconds.

An embodiment of the inventive method is therefore characterized by a new reconstruction of a modified image data record. What is involved therefore is not just a merging of different image data records. It is therefore much easier for the physician carrying out the examination or operation to locate and correctly position his medical apparatus (such as catheters, etc.).

Furthermore it is possible to check the selected position in terms of its functional interaction in the organ as a whole. Thus, for example, it may be precisely checked whether an aortic valve replacement is positioned at exactly the correct position in the LV outflow tract, so that it neither covers the coronary ostia with the aortic valve replacement nor impedes the function of the adjacent mitral valve.

A further advantage can be seen in the fact that the safety of interventional procedures can be significantly increased by improved imaging. Furthermore, the length of the procedures can be reduced as the physician can carry out the procedure more quickly as a result of improved imaging.

The radiation period and therefore the radiation dose overall may also be reduced.

Finally, reference should be made to the fact that the description of the invention and the example embodiments should basically not be taken to be limiting with regard to a specific physical implementation of the invention. For a relevant person skilled in the art it is particularly obvious that the invention can be partially or completely implemented in software and/or hardware and/or divided among a plurality of physical products, and in particular also computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

S static image
D dynamic image
10 carrying out vector analysis
12 providing movement information relating to the dynamic image
14 applying the vector analysis to the static image
16 displaying the modified static image
18 calculating module
M monitor

What is claimed is:

1. A display method for displaying body structures, the method comprising:
   acquiring, by one or more processors, a static image of a body structure in a high resolution;
   carrying out dynamic imaging, by the one or more processors, to acquire a dynamic image of the body structure in a resolution lower than the high resolution;
   carrying out vector analysis, by the one or more processors, on data records of the dynamic image to acquire a movement of the body structure, the vector analysis including analyzing the movement of the body structure in the dynamic image and generating a movement vector, the movement vector including a direction part and a speed part of the body structure;
   establishing a correlation between the static image and the dynamic image;
   applying, by the one or more processors, the vector analysis to the static image based on the establishing to calculate a modified static image with movement information of the body structure; and displaying, by one or more processors, the modified static image with associated movement information of the body structure.

2. The method as claimed in claim 1, wherein at least one of the static image is acquired pre-operatively and the dynamic image is acquired during a medical procedure.

3. The method as claimed in claim 2, wherein the displaying of the modified static image at least one of provides navigation information and is intended for location of medical instruments in the body structure within a framework of a medical procedure.

4. The method as claimed in claim 2, wherein at least one of the static image and the dynamic image is three-dimensional.

5. The method as claimed in claim 1, wherein the displaying of the modified static image at least one of provides navigation information and is intended for location of medical instruments in the body structure within a framework of a medical procedure.

6. The method as claimed in claim 1, wherein at least one of the static image and the dynamic image is three-dimensional.

7. The method as claimed in claim 1, wherein dynamic imaging is carried out in real time.

8. The method as claimed in claim 1, wherein the static image is computed tomography or a picture.

9. The method as claimed in claim 8, wherein the static image is a three-dimensional picture from interventional X-ray equipment.

10. The method as claimed in claim 1, wherein the dynamic image is an ultrasound image.

11. The method as claimed in claim 10, wherein the dynamic image is a three-dimensional ultrasound image.

12. The method as claimed in claim 1, wherein the application of vector analysis comprises:

allocating data of the dynamic image to the static image using reference points in correlation to a time axis.

13. The method as claimed in claim 12, wherein the allocation includes an interpolation of all matrix points for which no vector information exists.

14. The method as claimed in claim 1, wherein vector analysis is based on an Aldus Velocity Vector Imaging method.

15. The method as claimed in claim 1, wherein static imaging, dynamic imaging and the subsequent method steps can be carried out iteratively.

16. The method as claimed in claim 1, wherein the method is computer-assisted and is triggered and/or carried out semi-automatically.

17. The method as claimed in claim 1, wherein the method is only applied to surfaces of body structures, so only surfaces are dynamized.

18. A computer program that can be loaded or is loaded in a memory of a computer, with commands which are readable by the computer, for carrying out the method as claimed in claim 1 upon the commands being executed on the computer.

19. A computer readable medium including program segments for, when executed on a computer device, causing the computer device to implement the method of claim 1.

20. The method of claim 1, wherein the establishing includes, registering the static image with the dynamic image to establish the correlation.

21. The method of claim 1, wherein the acquiring acquires the static image using computed tomography and the carrying out dynamic imaging acquires the dynamic image using ultrasound.

22. A system for displaying body structures, the system comprising:

at least one static modality device to generate a static image in a high resolution;

at least one dynamic modality device to generate a dynamic image in a resolution lower than the high resolution;

at least one calculating module to carry out vector analysis on the generated dynamic image to acquire movement information of the body structure and establish a correlation between the static image and the dynamic image, wherein the calculating module is configured to apply the vector analysis to the generated static image based on the correlation to calculate a modified static image with movement information of the body structure, the vector analysis including analyzing the movement of the body structure in the dynamic image and generating a movement vector, the movement vector including a direction part and a speed part of the body structure; and at least one display device to display the modified static image with associated movement information of the body structure, as is provided by the calculating module.

23. A device for displaying body structures, the device comprising:

at least one calculating module to exchange data with a static modality device to acquire a static image in a high resolution and to exchange data with a dynamic modality device to acquire a dynamic image in a resolution lower than the high resolution, configured to carry out vector analysis on the static image to acquire movement information of the body structure, the vector analysis including analyzing the movement of the body structure in the dynamic image and generating a movement vector, the movement vector including a direction part and a speed part of the body structure, and establish a correlation between the static image and the dynamic image, wherein the calculating module is configured to apply a result of vector analysis to the static image based on the correlation to calculate a modified static image with movement information of the body structure to calculate a modified static image with movement information of the body structure.

* * * * *